US009885648B2

(12) United States Patent
Hirano et al.

(10) Patent No.: US 9,885,648 B2
(45) Date of Patent: Feb. 6, 2018

(54) PARTICLE DETECTING APPARATUS

(71) Applicant: TOSHIBA MEMORY CORPORATION, Tokyo (JP)

(72) Inventors: Masaki Hirano, Mie (JP); Yuichi Kuroda, Mie (JP); Kenichi Otsuka, Ishikawa (JP)

(73) Assignee: Toshiba Memory Corporation, Tokyo (JP)

( * ) Notice: Subject to any disclaimer, the term of this patent is extended or adjusted under 35 U.S.C. 154(b) by 0 days.

(21) Appl. No.: 15/064,713

(22) Filed: Mar. 9, 2016

(65) Prior Publication Data
US 2017/0074792 A1    Mar. 16, 2017

(30) Foreign Application Priority Data

Sep. 14, 2015 (JP) ................... 2015-181204

(51) Int. Cl.
*G01N 15/06* (2006.01)
*G01N 15/00* (2006.01)

(52) U.S. Cl.
CPC ... *G01N 15/065* (2013.01); *G01N 2015/0046* (2013.01)

(58) Field of Classification Search
CPC .............. G01N 21/53; G01N 15/1459; G01N 15/0205; G01N 15/0211; G01N 15/1434; G01N 21/51; G01N 15/1429; G01N 15/06; G01N 15/147; G01N 21/49; G01N 21/64; G01N 21/645; G01N 2015/0038; G01N 2015/1006
See application file for complete search history.

(56) References Cited

U.S. PATENT DOCUMENTS

| 3,790,760 | A | * | 2/1974 | Stiller .................... G06M 1/101 356/335 |
| 5,519,490 | A |   | 5/1996 | Nakata et al. |
| 5,579,107 | A | * | 11/1996 | Wright .................... G01N 1/286 241/39 |
| 6,194,487 | B1 | * | 2/2001 | Morimoto ................ B01J 2/006 523/205 |
| 6,741,350 | B2 | * | 5/2004 | Ikeda ..................... G01N 15/02 356/335 |

(Continued)

FOREIGN PATENT DOCUMENTS

JP      2013-190246    9/2013
JP      2014-002035    1/2014

*Primary Examiner* — Michael P Stafira
(74) *Attorney, Agent, or Firm* — Finnegan, Henderson, Farabow, Garrett & Dunner, L.L.P.

(57) ABSTRACT

A particle detecting apparatus has a condensing and growing unit to condense and grow a condensing component over particles contained in a gas while the gas imported through an inflow port is transported from a low temperature portion to a high temperature portion, a particle detector to detect a concentration of the particles contained in the gas discharged from an outflow port of the condensing and growing unit, a particle feeder to feed, to the inflow port of the condensing and growing unit, a test gas containing test particles whose particle diameter and the number of particles per unit volume are known, and a first determinator to determine whether a concentration of the test particles contained in the test gas detected by the particle detector has a predetermined value.

7 Claims, 6 Drawing Sheets

(56) References Cited

U.S. PATENT DOCUMENTS

| | | | | |
|---|---|---|---|---|
| 7,042,557 B2 * | 5/2006 | Yamaguchi | ........ | G01N 15/0205 221/180 |
| 7,242,473 B2 * | 7/2007 | Togawa | ............. | G01N 15/0205 356/335 |
| 7,349,084 B2 * | 3/2008 | Kusuzawa | ......... | G01N 15/0211 356/335 |
| 2013/0180321 A1 | 7/2013 | Shinohara et al. | | |

* cited by examiner

PARTICLE DETECTING APPARATUS

CROSS REFERENCE TO RELATED APPLICATIONS

This application is based upon and claims the benefit of priority from the prior Japanese Patent Application No. 2015-181204, filed on Sep. 14, 2015, the entire contents of which are incorporated herein by reference.

FIELD

The present invention relates to a particle detecting apparatus.

BACKGROUND

Particle detecting apparatuses that have been used hitherto often aim to detect particles having a particle diameter of at least 100 nm. However, particles floating in a clean room in the manufacturing process of, for example, a semiconductor device have a particle diameter smaller than 100 nm.

To detect particles having such a small particle diameter, the particles may be condensed with a condensing component, such as moisture, to increase the particle diameter before the detection.

To condense the particles with the condensing component, it is necessary to introduce the particles into a condensing and growing unit and transport the particles therethrough while the interior of the condensing and growing unit is in a supersaturation state.

It is, however, difficult to detect whether the interior of the condensing and growing unit attains a desired supersaturation level. The particles are not sufficiently condensed with the condensing component immediately after the measurement is started and, as a result of this, a significantly small number of particles are detected. Thus, the detection accuracy of the particles is deteriorated.

DETAILED DESCRIPTION OF THE INVENTION

According to one embodiment, a particle detecting apparatus has a condensing and growing unit to condense and grow a condensing component over particles contained in a gas while the gas imported through an inflow port is transported from a low temperature portion to a high temperature portion, a particle detector to detect a concentration of the particles contained in the gas discharged from an outflow port of the condensing and growing unit, a particle feeder to feed, to the inflow port of the condensing and growing unit, a test gas containing test particles whose particle diameter and the number of particles per unit volume are known, and a first determinator to determine whether a concentration of the test particles contained in the test gas detected by the particle detector has a predetermined value. When it is determined that the concentration of the test particles has the predetermined value, the condensing and growing unit imports in and transports the gas to be measured from the inflow port to the outflow port, and when it is determined that the concentration of the test particles has the predetermined value, the particle detector detects the concentration of the particles in the gas to be measured discharged from the outflow port.

Hereafter, embodiments of the present invention will be described in detail.

(First Embodiment)

Figure 1:
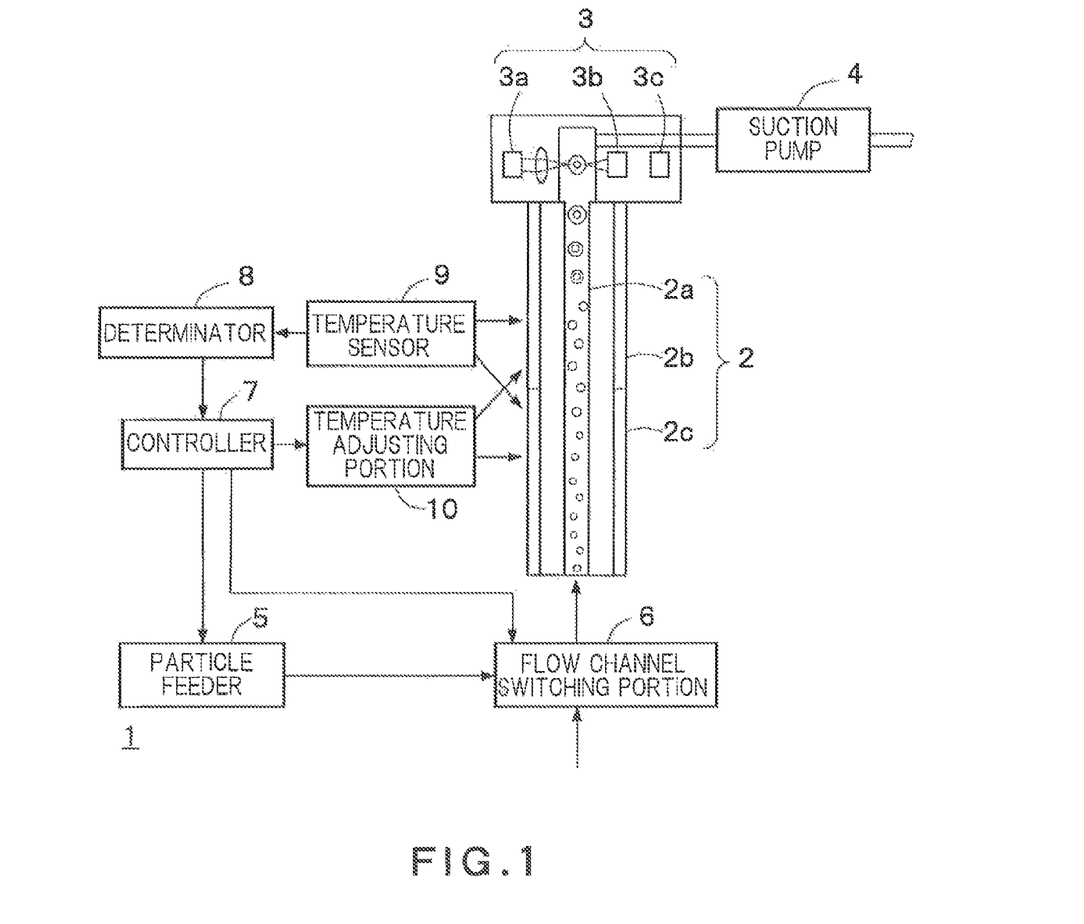
FIG. 1 is a block diagram schematically illustrating a structure of a particle detecting apparatus 1 according to a first embodiment.

FIG. 1 is a block diagram schematically illustrating a structure of a particle detecting apparatus 1 according to a first embodiment. The particle detecting apparatus 1 of FIG. 1 can be used to measure a concentration of particles floating in a clean room used for manufacturing a semiconductor device or the like. The particle detecting apparatus 1 of FIG. 1 can also be used for other purposes.

The particle detecting apparatus 1 of FIG. 1 includes a condensing and growing unit 2, a particle detector 3, a suction pump 4, a particle feeder 5, a flow channel switching portion 6, a controller 7, a determinator 8, a temperature sensor 9, and a temperature adjusting portion 10.

The condensing and growing unit 2 includes a condensing flow channel 2a that extends in a vertical direction in FIG. 1. The condensing flow channel 2a has an inflow port and an outflow port of gas and particles at the lower end and the upper end of the condensing flow channel 2a, respectively. A temperature in the condensing flow channel 2a is not fixed, and the upper part of the condensing flow channel 2a is set to have a higher temperature than in the lower part of the condensing flow channel 2a. Hereafter, the upper part of the condensing and growing unit 2 having a high temperature will be referred to as a high temperature portion 2b, while the lower part of the condensing and growing unit 2 having a low temperature will be referred to as a low temperature portion 2c. The temperature sensor 9 measures temperatures of the high temperature portion 2b and the low temperature portion 2c of the condensing and growing unit 2.

To provide a difference in temperature between the upper part and the lower part of the condensing flow channel 2a, the temperature adjusting portion 10 is disposed around the condensing flow channel 2a. The temperature adjusting portion 10 is in any shape, and a Peltier element, for example, may be used.

In the condensing flow channel 2a, predetermined fluid, such as moisture or alcohol, is in a supersaturation state. When particles pass through the condensing flow channel 2a, the particle become kernels and the condensing component, such as moisture, is condensed and grown around the kernels. Since the temperature of the upper portion of the condensing flow channel 2a is as high as the temperature of the lower portion, the particles are further condensed and grown as the particles are transported from the lower portion to the upper portion. Accordingly, the particles discharged from the outflow port of the condensing flow channel 2a have the particle diameter significantly larger than the particle diameter of the particles having flowed into the inflow port of the condensing flow channel 2a.

The particle detector 3 optically detects the number of particles discharged from the outflow port of the condensing flow channel 2a to detect the number of particles per unit volume, that is, the concentration of the particles. The particle detector 3 includes a light ejecting portion 3a, a light receiving portion 3b, and a counter 3c. The light ejecting portion 3a ejects light, such as light from a laser or an LED. The light receiving portion 3b receives light ejected from the light ejecting portion 3a. When the particles impinge on light ejected from the light ejecting portion 3a, the light is scattered and the light intensity of the light receiving portion 3b is changed. The number of times that the light intensity is changed is measured by the counter 3c to thereby count the number of particles.

The suction pump 4 suctions the atmosphere in the condensing and growing unit 2 and the particle detector 3 at a predetermined pressure. The particles having entered the condensing flow channel 2a are transported from the lower portion to the upper portion to pass through the particle detector 3, and then is guided to the suction pump 4.

The particle feeder 5 feeds, to the condensing and growing unit 2, a test gas that contains test particles whose particle diameter and the number of particles per unit volume are already known. The test particles may be hydrophilic particles, such as sodium chloride, or may be hydrophobic particles, such as oleic acid. Alternatively, the test particles may have an intermediate nature between the hydrophilic and hydrophobic natures, such as polystyrene latex.

In the present embodiment, as will be described later, the test gas is fed to the condensing and growing unit 2 before the original measurement of the concentration of particles is started. When the test particles are detected by the particle detector 3, the original measurement of the concentration of the particles is started. It is, therefore, desirable to choose hardly detectable particles as the test particles. The reason for this is that, if the test particles are hardly detectable, but are correctly detected by the particle detector 3, it is determined that the interior of the condensing flow channel 2a is supersaturated and the stable particle concentration measurement is possible. Hydrophobic particles are less capable of condensing and growing moisture or the like than hydrophilic particles. It is, therefore, desirable to use the hydrophobic particles as the test particles from the viewpoint of difficulty of detection.

The flow channel switching portion 6 switches between the atmosphere to be measured, which is originally intended to be measured, and the test gas, and feeds either one to the condensing and growing unit 2. The flow channel switching portion 6 may be implemented by, for example, a valve.

The controller 7 controls the temperature adjusting portion 10 such that the condensing flow channel 2a is supersaturated, based on the temperature detected by the temperature sensor 9. The controller 7 also controls timing for feeding the test gas from the particle feeder 5 and timing for switching the flow channel switching portion 6.

Figure 2:
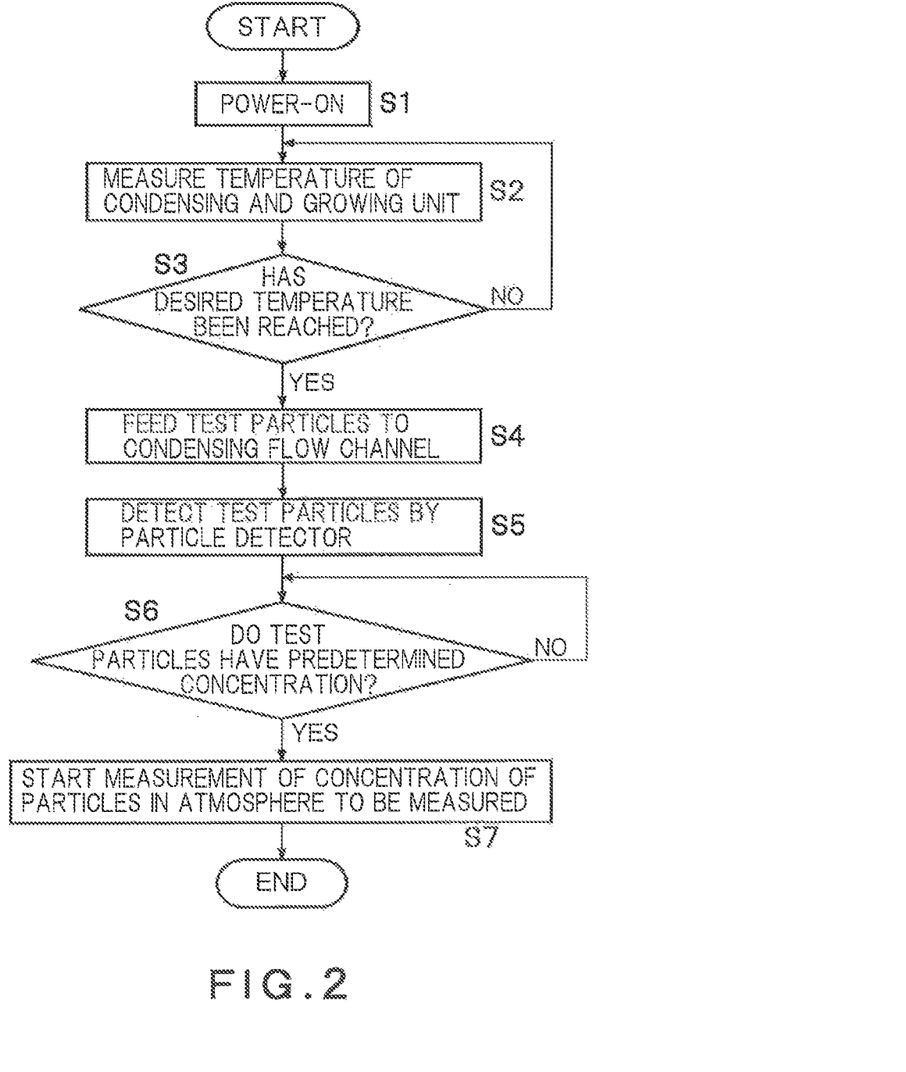
FIG. 2 is a flowchart illustrating a processing operation of the particle detecting apparatus 1 of FIG. 1.

FIG. 2 is a flowchart illustrating a processing operation of the particle detecting apparatus 1 of FIG. 1. First, an operator turns on a power supply of the particle detecting apparatus 1 (step S1). Accordingly, the controller 7 performs temperature adjustment of the high temperature portion 2b and the low temperature portion 2c of the condensing and growing unit 2 by using the temperature adjusting portion 10.

The temperature sensor 9 measures the temperatures of the high temperature portion 2b and the low temperature portion 2c of the condensing and growing unit 2 (step S2). The determinator 8 determines whether the high temperature portion 2b and the low temperature portion 2c have individually reached a desired temperature (step S3, a second determinator). If the desired temperatures have not been reached, the process returns to step S2 and waits until the desired temperature is reached by, for example, controlling the temperature adjusting portion 10.

When the high temperature portion 2b and the low temperature portion 2c of the condensing and growing unit 2 have reached the desired temperatures, it is determined that the interior of the condensing flow channel 2a has reached a supersaturation state. The particle feeder 5 then feeds the test gas when it is determined in step S3 that the high temperature portion 2b and the low temperature portion 2c have reached the desired temperatures (step S4). The flow channel switching portion 6 guides the test gas from the particle feeder 5 to the inflow port in the condensing flow channel 2a. The diameters of the test particles increase as the moisture or the like is condensed to grow the particles while the test particles are transported upward through the condensing flow channel 2a. The test particles are then discharged from the outflow port of the condensing flow channel 2a, and detected by the particle detector 3 (step S5).

Next, it is determined whether the concentration of the test particles detected by the particle detector 3 is a predetermined concentration (step S6, a first determinator). If the detected concentration is not the predetermined concentration, the process returns to step S5. If the detected concentration is the predetermined concentration, it is determined that the measurement is ready, and the flow channel switching portion 6 is switched to introduce the gas to be measured into the condensing flow channel 2a to start the original measurement of the concentration of the particles (step S7).

When the concentration of the test particles has reached the predetermined concentration in step S6, indicating that the supersaturation level of moisture or the like has sufficiently increased in the condensing flow channel 2a, it is considered that the particles contained in the atmosphere to be measured can be condensed and grown securely. When it is determined in step S6 that the concentration of the test particles has reached the predetermined concentration, the original measurement of the concentration of the particles is started.

Figure 3:
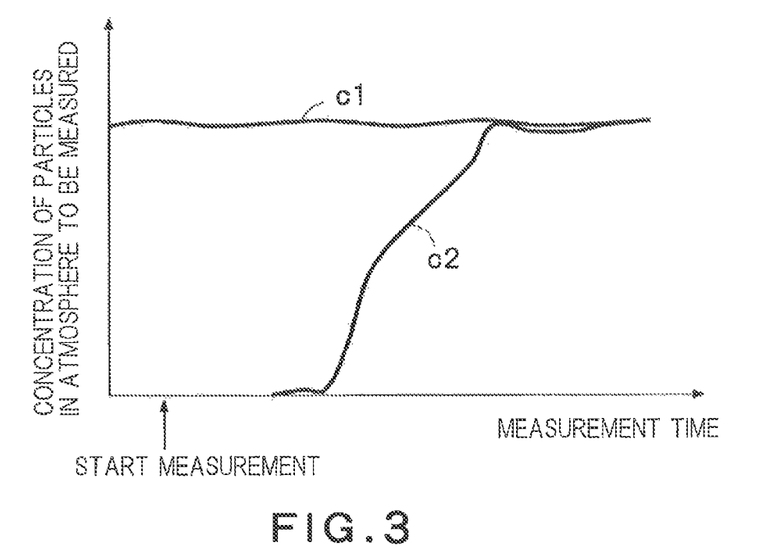
FIG. 3 is a graph plotting the concentration of particles that changes over time in a gas to be measured.

If the processing of steps S4 to S7 of FIG. 2 is skipped and the measurement of the originally intended particle concentration is started only when it is determined in step S3 that the high temperature portion 2b and the low temperature portion 2c of the condensing and growing unit 2 have individually reached the desired temperature, a result will be obtained as illustrated in FIG. 3. The abscissa of the graph in FIG. 3 represents the measurement time and the ordinate represents the concentration of particles in the atmosphere to be measured. A curve c1 of FIG. 3 indicates a reference measurement value that is originally intended to be measured. A curve c2 indicates a concentration of particles detected by the particle detector 3.

As indicated by the curve c2 of FIG. 3, the particle detector 3 hardly detects particles for some time after the measurement of the concentration of the particles is started. It takes time till the particle detector 3 detects the concentration of the particles correctly, if the processing of steps S4 to S7 of FIG. 2 is skipped. A reason for this may be that the interior of the condensing flow channel 2a has not been in a complete supersaturation state immediately after the measurement is started.

In contrast, the original measurement of the concentration of the particles in the atmosphere to be measured is started only when the concentration of the test particles, as well as the temperature of the condensing flow channel 2a, is correctly detected in the present embodiment, As a result of this, the concentration of the particles can be measured correctly by the particle detector 3 immediately after the start of the measurement. It can be seen from the comparison with the curve c2 of FIG. 3 that the concentration of particles that is obtained immediately after the start of the measurement is approximately the same as the reference measurement value.

In the first embodiment, when the temperature of the interior of the condensing flow channel 2a has reached the desired temperature, the test particles are fed into the condensing flow channel 2a and the particle detector 3 measures the concentration of the test particles. When the concentration reaches the predetermined concentration, the original measurement of the concentration of particles in the atmosphere to be measured is started. The measurement of the concentration of particles in the atmosphere to be measured is started when the moisture or the like in the condensing flow channel 2a reaches a suitable supersaturation level. Thus, the concentration of the particles can be measured stably immediately after the start of the measurement.

(Second Embodiment)

Figure 4:
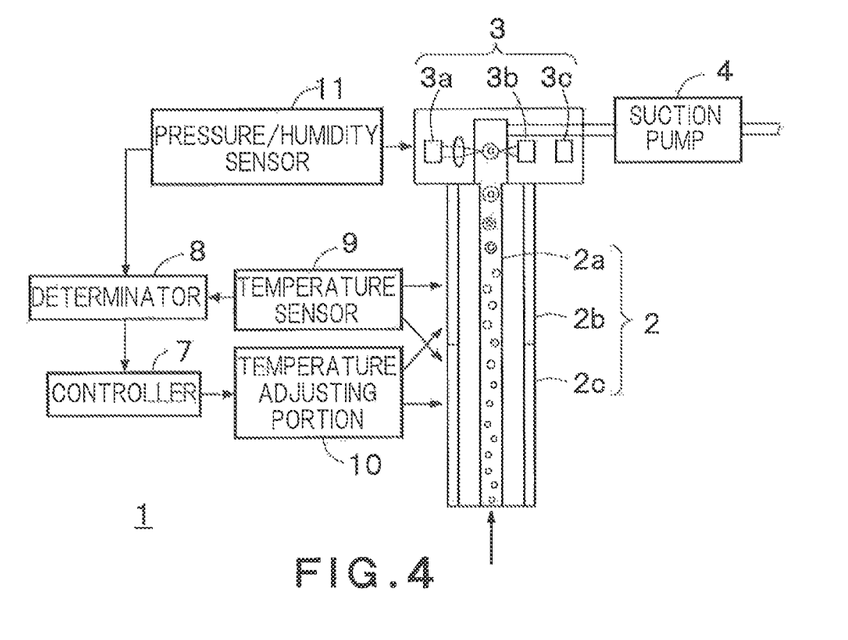
FIG. 4 is a block diagram schematically illustrating a structure of the particle detecting apparatus 1 according to a second embodiment.

FIG. 4 is a block diagram schematically illustrating the structure of the particle detecting apparatus 1 according to a second embodiment. In FIG. 4, the same reference signs are given to constituent elements that are common to those of FIG. 1, and only a difference will mainly be described below.

The particle detecting apparatus 1 of FIG. 4 includes a pressure/humidity sensor (atmosphere detector) 11, and the particle feeder 5 is removed. Other constituent elements are similar to those of FIG. 1.

The pressure/humidity sensor 11 measures at least one of a pressure and humidity in the atmosphere near the outflow port of the condensing flow channel 2a. The pressure/humidity sensor 11 may be implemented as a pressure sensor or a humidity sensor, or both the pressure sensor and the humidity sensor may be provided.

The pressure and humidity in the atmosphere near the outflow port of the condensing flow channel 2a largely affects the supersaturation level in the condensing flow channel 2a. That is the supersaturation level in the condensing flow channel 2a is accurately estimated by measuring at least one of the pressure and the humidity of the atmosphere near the outflow port of the condensing flow channel 2a. Specifically, if at least one of the pressure and the humidity is equal to or larger than a predetermined value, it is determined that the supersaturation level in the condensing flow channel 2a has reached a value which is suitable for the measurement of the concentration of particles.

Since the particle detector 3 measures the particles contained in the atmosphere near the outflow port of the condensing flow channel 2a, it is determined whether the particle detector 3 can correctly detect the concentration of the particles by measuring the pressure or humidity near the particle detector 3.

Figure 5:
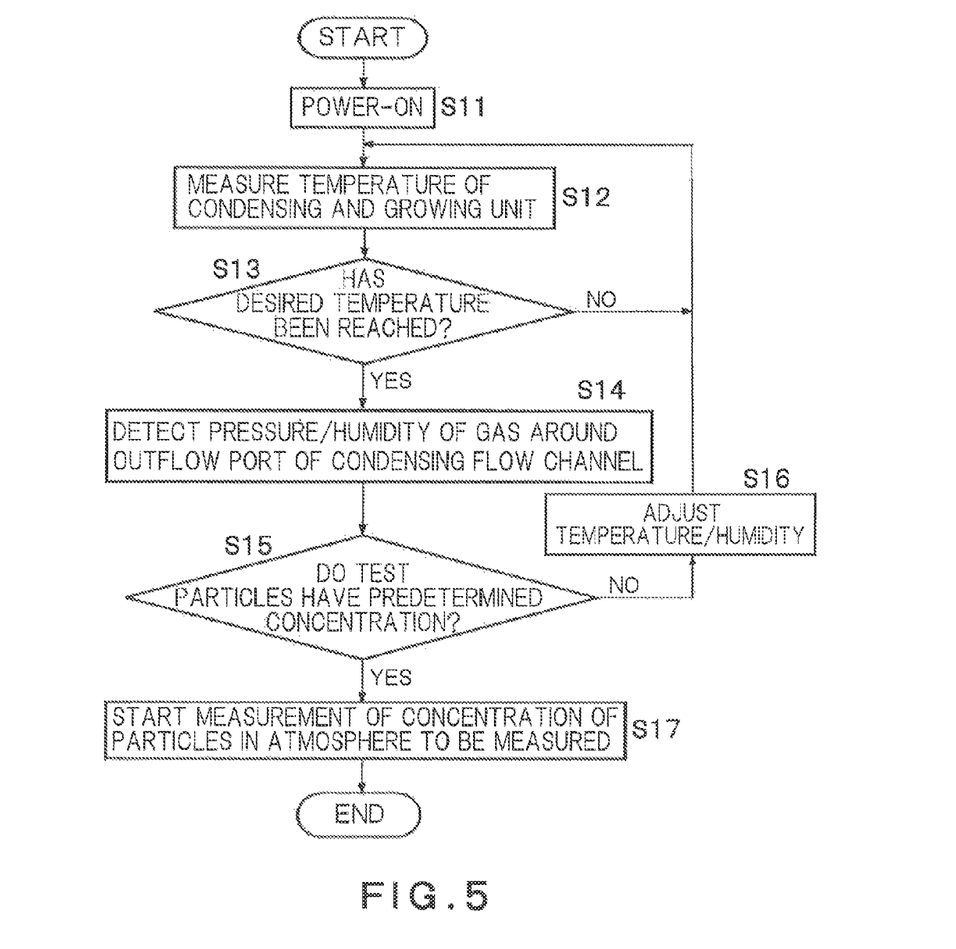
FIG. 5 is a flowchart illustrating a processing operation of the particle detecting apparatus 1 of FIG. 4.

FIG. 5 is a flowchart illustrating the processing operation of the particle detecting apparatus 1 of FIG. 4. The processing of steps S11 to S13 is the same as steps S1 to S3 of FIG. 2. When it is determined in step S13 that the high temperature portion 2b and the low temperature portion 2c of the condensing and growing unit 2 have individually reached the desired temperature, the pressure/humidity sensor 11 detects at least one of the pressure and the humidity of the atmosphere near the outflow port of the condensing flow channel 2a (step S14).

After that, it is determined whether at least one of the detected pressure and the detected humidity has reached a predetermined value (step S15, a second determinator). If the detected value has not reached the predetermined value, the temperature adjusting portion 10 may adjust the temperature of at least one of the high temperature portion 2b and the low temperature portion 2c of the condensing and growing unit 2. Alternatively, the temperature adjusting portion 10 may adjust the humidity of the atmosphere that enters through the inflow port of the condensing flow channel 2a (step S16). Subsequently, the process proceeds to step S12.

In step S15, if it is determined that at least one of the pressure and the humidity has reached the predetermined value, the original measurement of the concentration of the particles in the atmosphere to be measured is started (step S17).

In the second embodiment, at least one of the pressure and the humidity of the atmosphere near the particle detector 3, that is, near the outflow port of the condensing flow channel 2a is detected, whereby the supersaturation level is estimated accurately in the condensing flow channel 2a. Thus, it is correctly determined whether the supersaturation level has reached an appropriate value for the measurement of the concentration of the particles.

(Third Embodiment)

A third embodiment is provided as a combination of the first and second embodiments.

Figure 6:
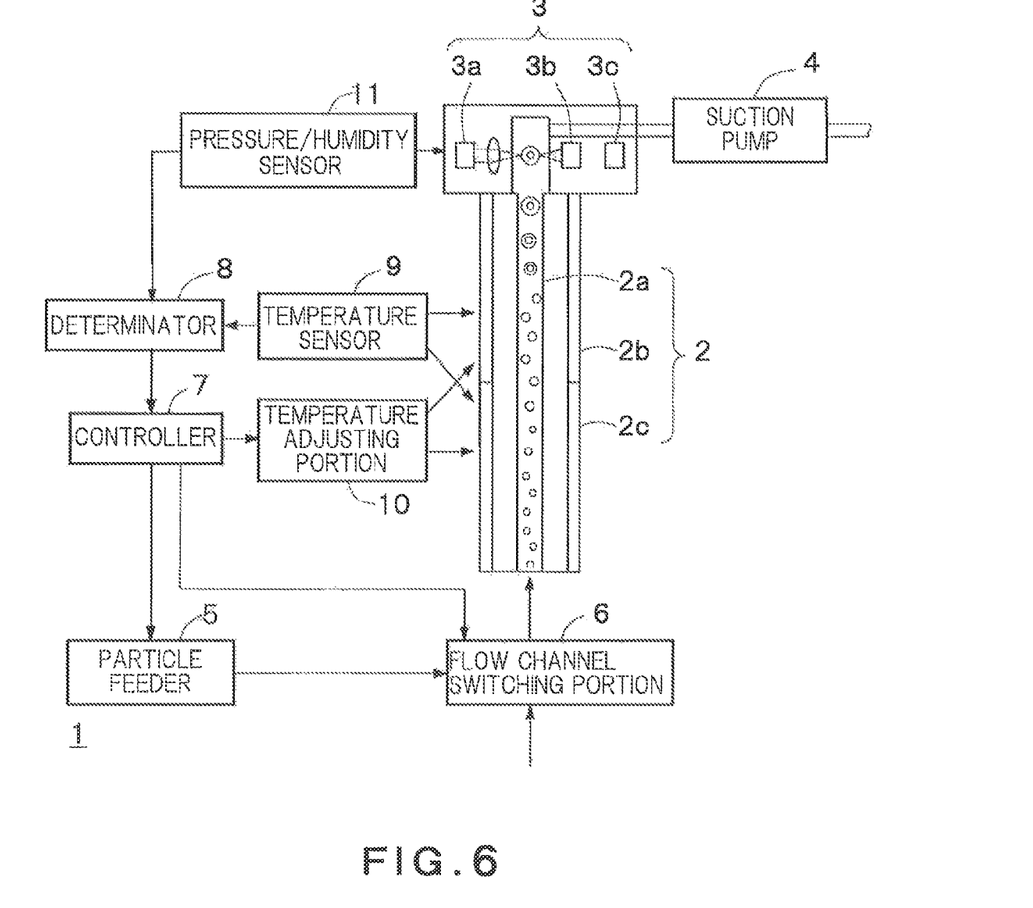
FIG. 6 is a block diagram schematically illustrating a the structure of a particle detecting apparatus 1 according to a third embodiment.

FIG. 6 is a block diagram schematically illustrating the structure of the particle detecting apparatus 1 according to a third embodiment. In FIG. 6, the same reference signs are given to constituent elements that are common to those of FIGS. 1 and 4, and only a difference will mainly be described below.

The particle detecting apparatus 1 of FIG. 6 includes the particle detector 3 of FIG. 1 and the pressure/humidity sensor 11 of FIG. 4. Other constituent elements of the structure are similar to those of FIGS. 1 and 4.

In the particle detecting apparatus 1 of FIG. 6, when the high temperature portion 2b and the low temperature portion 2c of the condensing and growing unit 2 have individually reached the desired temperature, while at least one of the pressure and the humidity of the atmosphere near the outflow port of the condensing flow channel 2a has reached the predetermined value, the test gas containing the test particles is fed into the condensing flow channel 2a. When the concentration of the test particles reaches the predetermined value, the original measurement of the concentration of the particles in the atmosphere originally intended to be measured is started.

Figure 7:
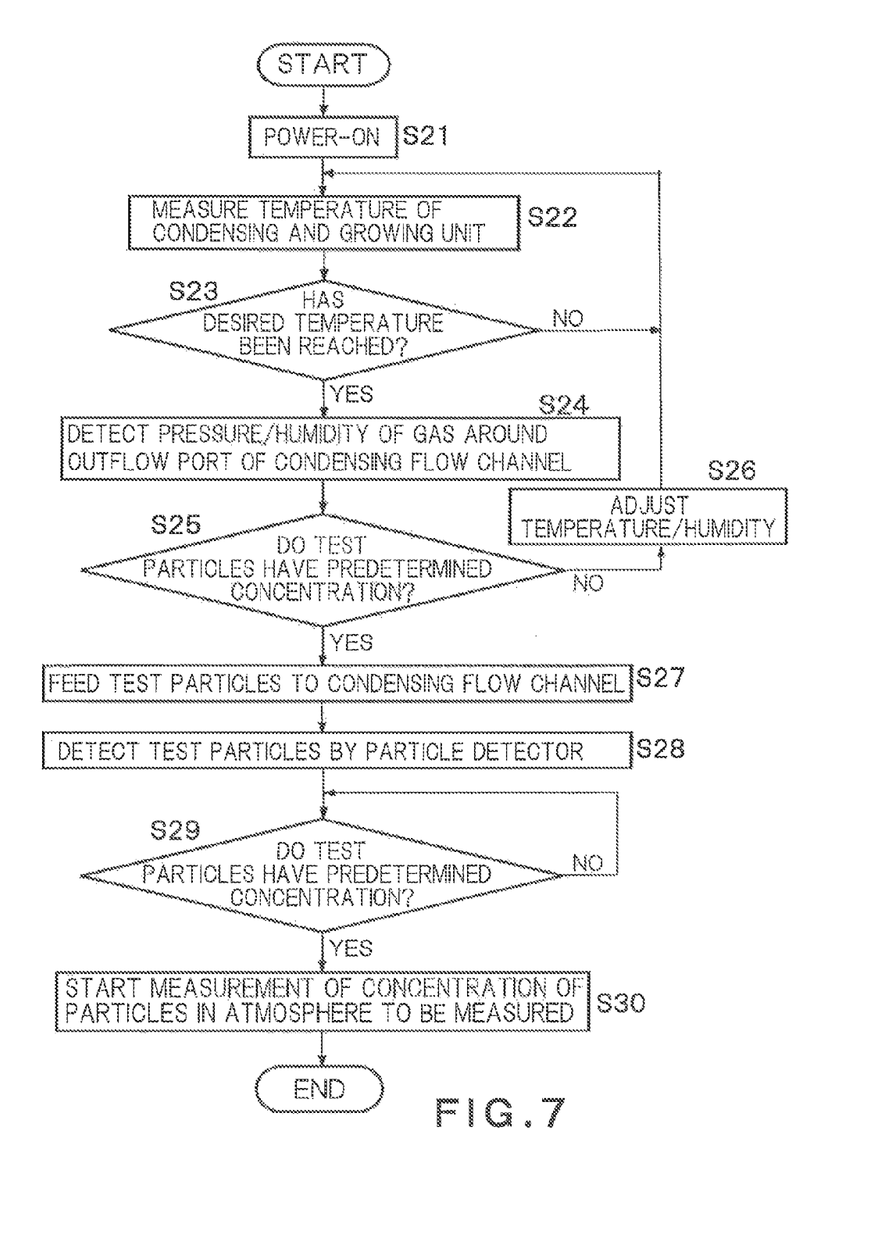
FIG. 7 is a flowchart illustrating a processing operation of the particle detecting apparatus 1 of FIG. 6.

FIG. 7 is a flowchart illustrating the processing operation of the particle detecting apparatus 1 of FIG. 6. Steps S21 to S26 of FIG. 7 are similar to those of steps S11 to S16 of FIG. 5. In step S25, if at least one of the pressure and the humidity of the atmosphere near the outflow port of the condensing flow channel 2a has reached the predetermined value, the particle feeder 5 feeds the test gas to the condensing flow channel 2a, as in steps S4 to S7 of FIG. 2. After that, when the concentration of the test particles detected by the particle detector 3 reaches the predetermined value, the original measurement of the concentration of the particles in the atmosphere to be measured is started (steps S27 to S30, a third determinator).

In the third embodiment, whether the original measurement of the concentration of the particles in the atmosphere to be measured is started is determined in accordance with the measurement result of the temperature of the condensing flow channel 2a, the detection result of at least one of the pressure and the humidity near the outflow port of the condensing flow channel 2a, and the detection result of the concentration of the test particles. It is, therefore, possible to more accurately estimate the supersaturation level of the condensing flow channel 2a than in the first and second embodiments. The measurement of the concentration of the particles in the originally intended atmosphere to be measured is started at optimal timing.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A particle detecting apparatus, comprising:
   a condensing and growing unit to condense and grow a condensing component over particles contained in a gas while the gas imported through an inflow port is transported from a low temperature portion to a high temperature portion;
   a particle detector to detect a concentration of the particles contained in the gas discharged from an outflow port of the condensing and growing unit;
   a particle feeder to feed, to the inflow port of the condensing and growing unit, a test gas containing test particles whose particle diameter and the number of particles per unit volume are known; and
   a first determinator to determine whether a concentration of the test particles contained in the test gas detected by the particle detector has reached a predetermined value, wherein
   when it is determined by the first determinator that the concentration of the test particles has reached the predetermined value, the condensing and growing unit imports in and transports the gas to be measured from the inflow port to the outflow port, and
   when it is determined by the first determinator that the concentration of the test particles has reached the predetermined value, the particle detector starts detecting the concentration of the particles in the gas to be measured discharged from the outflow port.

2. The particle detector according to claim 1, further comprising:
   a second determinator to determine whether a temperature of the condensing and growing unit reaches a predetermined temperature,
   wherein the particle feeder feeds the test particles to the inflow port of the condensing and growing unit when the second determinator determines that the temperature of the condensing and growing unit has reached the predetermined temperature.

3. A particle detecting apparatus, comprising:
   a condensing and growing unit to condense and grow a condensing component over particles contained in a gas while the gas imported through an inflow port is transported from a low temperature portion to a high temperature portion;
   a particle detector to detect a concentration of the particles discharged from an outflow port of the condensing and growing unit;
   an atmosphere detector to detect at least one of a pressure and humidity of the gas discharged from the outflow port of the condensing and growing unit; and
   a first determinator to determine whether a detection value detected by the atmosphere detector has reached a predetermined threshold value, wherein
   the particle detector detects a concentration of the particles in the gas discharged from the outflow port when it is determined that the detection value detected by the atmosphere detector has reached the threshold value.

4. The particle detecting apparatus according to claim 3, further comprising:
   a second determinator to determine whether a temperature of the condensing and growing unit has reached a predetermined temperature,
   wherein the atmosphere detector detects at least one of a pressure and humidity of the gas discharged from the outflow port of the condensing and growing unit when the second determinator determines that the temperature of the condensing and growing unit has reached the predetermined temperature.

5. The particle detecting apparatus according to claim 4, further comprising:
   a particle feeder to feed, to an inflow port of the condensing and growing unit, test particles whose particle diameter and the number of particles per unit volume are known when the first determinator determines that a detection value detected by the atmosphere detector has reached the threshold value; and
   a third determinator to determine whether a concentration of the test particles detected by the particle detector has reached a predetermined value, wherein
   the condensing and growing unit imports a gas to be measured from the inflow port and transports the gas to the outflow port when it is determined that the detection value detected by the atmosphere detector has reached the threshold value and the concentration of the test particles has the predetermined value, and
   the particle detector detects the concentration of the particles in the gas to be measured discharged from the outflow port when it is determined that the detection value detected by the atmosphere detector has reached the threshold value and the concentration of the test particles has the predetermined value.

6. The particle detector according to claim 1, wherein the test particles are made of sodium chloride, oleic acid, or polystyrene latex.

7. The particle detector according to claim 5, wherein the test particles are made of sodium chloride, oleic acid, or polystyrene latex.

* * * * *